(12) United States Patent
O'Grady et al.

(10) Patent No.: US 9,124,979 B2
(45) Date of Patent: Sep. 1, 2015

(54) METHOD AND APPARATUS FOR SENSORY SUBSTITUTION

(71) Applicant: NATIONAL UNIVERSITY OF IRELAND MAYNOOTH, County Kildare (IE)

(72) Inventors: Paul O'Grady, Dublin (IE); Ross O'Neill, Dublin (IE); Barak A. Pearlmutter, Dublin (IE)

(73) Assignee: National University of Ireland, Maynooth, County Kildare (IE)

( * ) Notice: Subject to any disclaimer, the term of this patent is extended or adjusted under 35 U.S.C. 154(b) by 0 days.

(21) Appl. No.: 14/012,539

(22) Filed: Aug. 28, 2013

(65) Prior Publication Data
US 2014/0079251 A1    Mar. 20, 2014

Related U.S. Application Data

(63) Continuation of application No. PCT/EP2011/070595, filed on Nov. 21, 2011.

(30) Foreign Application Priority Data

Nov. 23, 2010  (IE) .................................. S2010/0739

(51) Int. Cl.
*H04R 25/00* (2006.01)
*H04R 1/46* (2006.01)
(Continued)

(52) U.S. Cl.
CPC *H04R 1/46* (2013.01); *A61F 11/04* (2013.01); *H04R 25/75* (2013.01); *H04R 1/025* (2013.01); *H04R 2460/13* (2013.01)

(58) Field of Classification Search
USPC ................................................. 381/151, 395
See application file for complete search history.

(56) References Cited

U.S. PATENT DOCUMENTS

| 6,047,074 A | 4/2000 | Zoels et al. |
| 6,048,305 A | 4/2000 | Bauman et al. |

(Continued)

FOREIGN PATENT DOCUMENTS

WO    WO2009061520 A1    5/2009

OTHER PUBLICATIONS

C.E. Shannon, "A Mathematical Theory of Communication", Reprinted with corrections from the Bell System Technical Journal, Oct. 1948; pp. 1-55, vol. 27, pp. 379-423, 623-656.

(Continued)

*Primary Examiner* — Davetta W Goins
*Assistant Examiner* — Amir Etesam
(74) *Attorney, Agent, or Firm* — Schmeiser, Olsen & Watts LLP; Lowell W. Gresham; Steven J. Miller, MD.

(57) ABSTRACT

An apparatus and method for use in treating tinnitus, employs a sound processing unit, a tactile unit, and an interface therebetween. The tactile unit comprises an array of stimulators each of which can be independently actuated to apply a tactile stimulus to a subject, and an input for receiving a plurality of actuation signals from the interface and directing individual actuation signals to individual stimulators. The sound processing unit receives an audio signal at an input, analyses the signal with a digital signal processor to generate the actuation signals which are representative of the audio signal, and provides the plurality of actuation signals to the interface. In a preferred embodiment the digital signal processor divides the audio signal into a series of frames in the time domain, performs a transform on each frame to generate a set of coefficients representing said frame, and maps the set of coefficients to a set of actuation signals to be applied to the array.

17 Claims, 4 Drawing Sheets

(51) Int. Cl.
*A61F 11/04* (2006.01)
*H04R 1/02* (2006.01)

(56) References Cited

U.S. PATENT DOCUMENTS

| | | | |
|---|---|---|---|
| 6,198,971 | B1 | 3/2001 | Leysieffer |
| 6,259,951 | B1 | 7/2001 | Kuzma et al. |
| 6,682,472 | B1 | 1/2004 | Davis |
| 6,735,315 | B1 * | 5/2004 | Ifukube et al. ............ 381/70 |
| 6,792,324 | B2 * | 9/2004 | Trinkel ............ 700/94 |
| 2002/0035309 | A1 | 3/2002 | Leysieffer |
| 2005/0043646 | A1 | 2/2005 | Viirre et al. |
| 2007/0050212 | A1 | 3/2007 | Kearby et al. |
| 2007/0133832 | A1 | 6/2007 | DiGiovanni et al. |
| 2007/0156063 | A1 | 7/2007 | Zoth et al. |
| 2007/0270920 | A1 | 11/2007 | Turner et al. |
| 2009/0270673 | A1 | 10/2009 | Abolfathi et al. |
| 2009/0306741 | A1 | 12/2009 | Hogle et al. |

OTHER PUBLICATIONS

Fred Attneave, "Some Informational Aspects of Visual Perception", Psychological Review, Jun. 26, 1954, pp. 183-193, vol. 61, No. 3.

Dr. H.B. Barlow, "Sensory Mechanisms, The Reduction of Redundancy, and Intelligence", National Physical Laboratory, Presented at a Symposium on the Mechanization of Thought Process, Nov. 24-27, 1958, No. 10, pp. 1-25, England.

H.B. Barlow, "Possible Principles Underlying the Transformations of Sensory Messages", Physiological Laboratory, 1961, pp. 217-234, Cambridge University.

Horace Barlow, "Redundancy Reduction Revisited", Physiological Laboratory, Nov. 31, 2000, pp. 241-253, Computation in Neural Systems 12, Cambridge.

Karl Pearson, "On Lines and Planes of Closest Fit to Systems of Points in Space", 1901, pp. 559-572, Philosophical Magazine 2, London.

Pierre Comon, "Independent Component Analysis, A New Concept?", Aug. 24, 1992, pp. 287-314, Elsevier Science, Signal Processing 36, France.

Joseph J. Atick et al., "Understanding Retinal Color Coding from First Principles", School of Natural Sciences, 119, pp. 559-572, Neural Computation 4, 1992, New Jersey.

Joseph J. Atick, "Could Information Theory Provide an Ecological Theory of Sensory Processing?", School of Natural Sciences, Dec. 31, 1991, pp. 213-251, New Jersey.

Joseph J. Atick et al., "Towards a Theory of Early Visual Processing", Journal Neural Computation, 1990, pp. 308-320, vol. 2 Issue 3, Cambridge.

Aapo Hyvarinen et al., "A Fast Fixed-Point Algorithm for Independent Component Analysis", Neural Computation 9, 1997, pp. 1483-1492, Helsinki University of Technology, Finland.

Daniel D. Lee et al., "Learning the Parts of Objects by Non-Negative Matrix Factorization", Department of Brain and Cognitive Sciences, Massachusetts Institute of Technology, Oct. 21, 1999, pp. 788-791, Nature vol. 401, Massachusetts.

Daniel D. Lee et al., "Algorithms for Non-Negative Matrix Factorization", Advances in neural information processing systems, 2001, pp. 1-7, Massachusetts.

Anthony J. Bell et al., "An Information—Maximisation Approach to Blind Separation and Blind Deconvolution", Neural Computation 7, 6, Feb. 1995, pp. 1-38, San Diego, CA.

H.B. Barlow, "Unsupervised Learning", Neural Computation 1, 1989, pp. 295-311, England.

Pentti Paatero et al., "Positive Matrix Factorization: A Non-Negative Factor Model With Optimal Utilization of Error Estimates of Data Values", Environmetrics, 1994, vol. 5, pp. 111-126, Finland.

Craig W. Newman, PhD. et al., "Development of the Tinnitus Handicap Inventory", Arch Otolaryngol Head Neck Surg., Feb. 1996, vol. 122, pp. 143-148, New Haven, CT.

Peter H. Wilson et al., "Tinnitus Reaction Questionnaire: Psychometric Properties of a Measure of Distress Associated With Tinnitus", Journal of Speech and Hearing Research, Feb. 1991, vol. 34, pp. 197-201, Australia.

Michael Zibulevsky et al., "Blind Source Separation by Sparse Decomposition in a Signal Dictionary", Neural Computation 13, 2001, pp. 863-882, Massachusetts.

Vessela TZ Krasteva et al., "Estimation of Current Density Distribution Under Electrodes for External Defibrillation", BioMedical Engineering Online 2002, 1:7 , pp. 1-13, http://www.biomedical-engineering-online.com/contenl/1/1f7.

European Patent Office, Examination Report of Application No. 11 793 370.5 with PCT International Search Report of International Application No. PCT/EP2011/070595, Dec. 10, 2014, pp. 1-9, Munich, Germany.

Patent Cooperation Treaty, International Search Report for PCT/US08/12687; Jan. 2, 2009, pp. 1-5, ISA.

Mutebutton, "The Perception of Imaginary Sound", Video Presentation Transcript, http://vimeo.com/16020279.

Patent Cooperation Treaty, Written Opinion of the ISA for PCT/EP2011/070595.

* cited by examiner

METHOD AND APPARATUS FOR SENSORY SUBSTITUTION

TECHNICAL FIELD

This invention relates to methods and apparatuses for sensory substitution, with particular application in the treatment of tinnitus.

BACKGROUND ART

Tinnitus is an abnormal neurological behaviour arising from loss of signal through the ear. While the precise causes of tinnitus are not fully understood, certain analogies are employed to describe the likely causes. For example, it is thought that tinnitus is often caused by a physical hearing impediment such as damage to the hairs in the cochlea. In an attempt to compensate for the missing audio information the brain raises amplification and the gains in recurrent loops to such an extent that false signals are generated, similar in principle to the ringing noise that can occur when the volume of an audio amplifier in an auditorium is raised too high. Alternatively, one may imagine an electrical water pump whose water supply is suddenly restricted. The pump oscillates and vibrates in a desperate attempt to compensate for the loss of input. Tinnitus may be thought of as essentially arising from the same types of mechanism: loss of signal through the ear results in increased spontaneous and oscillatory activity in the associated neurons in the brain. This activity is perceived as illusory sound by the sufferer.

Tinnitus sufferers are significantly more likely to perceive an illusory audio after-effect known as the Zwicker Tone. The Zwicker Tone is induced by exposing the individual to broadspectrum noise (20 Hz-20 KHz) with a spectral gap (silence) at an arbitrary frequency. When the noise is removed the individual perceives a 'ringing' at the frequency of the spectral gap. This suggests that in order to compensate for the unequal cochlear sensitivity across frequencies, the brain introduces frequency dependent sensitivity or gain similar to a 'graphic equalizer' on a stereo. At the frequencies that our cochlea is less sensitive, the brain increases the gain in that frequency band to compensate. In frequency bands where sensitivity falls below a minimum threshold, the brain increases the gain to pathological levels. This manifests as illusory noise, ringing or even chaotic oscillation, the most commonly described effects of Tinnitus.

A very large number of treatments have been proposed for tinnitus, including radiosurgery, direct stimulation of the auditory nerves, pharmacological treatments, psychological treatments, and treatment by playing external sounds to the patient. While many such treatments provide relief in some groups of patients, at present there is no reliable treatment for all patients, and the present invention aims to provide a further alternative approach.

DISCLOSURE OF THE INVENTION

There is provided an apparatus for use in treating tinnitus, comprising a sound processing unit, a tactile unit, and an interface therebetween, wherein:
  said tactile unit comprises an array of stimulators each of which can be independently actuated to apply a tactile stimulus to a subject, and an input for receiving a plurality of actuation signals from said interface and directing individual actuation signals to individual stimulators; and
  said sound processing unit comprises:
    an input for receiving an audio signal;
    a digital signal processor operable to analyse said audio signal and generate said plurality of actuation signals therefrom which are representative of said audio signal; and
    an output for receiving said plurality of actuation signals from said digital signal processor and providing said plurality of actuation signals to said interface.

Preferably, said digital signal processor is further operable to generate said plurality of actuation signals as a time-varying sequence of output array patterns, wherein each output array pattern comprises a set of actuation signals to be applied to the array for a discrete period of time, representative of a discrete time sample of the input signal.

According to one embodiment, said digital signal processor is programmed to analyse said audio signal by dividing said audio signal into a series of frames in the time domain, performing a transform on each frame to generate a set of coefficients representing said frame, and mapping said set of coefficients to a set of actuation signals to be applied to the array.

Said transform performed on each frame is preferably selected from a fourier transform, a short-time fourier transform (STFT), a wavelet transform, a curvelet transform, a gammatone transform and a zak transform.

More preferably, said transform is a fourier transform or a short-time fourier transform, and wherein said signal is sampled at a sampling rate of between 4 kHz and 12 kHz, more preferably between 6 kHz and 10 kHz, and most preferably about 8 kHz.

Suitably, said time-varying series of frames may overlap with one another.

The start of each frame is preferably offset from the start of the preceding frame by between 10 and 20 ms, more preferably by 12-18 ms, and most preferably by about 16 ms.

The processor is preferably programmed to employ a frame length of from 18 to 164 ms, more preferably from 50 to 150 ms, and most preferably 64 or 128 ms.

The set of coefficients preferably represent the signal in the frequency domain, and the coefficients are mapped to the actuation signals such that coefficients representing similar frequencies are mapped to actuation signals directed to stimulators which are physically close to one another in said array.

More preferably, the coefficients representing neighbouring frequencies are mapped to actuation signals directed to stimulators which are physically adjacent to one another.

In alternative embodiments, the digital signal processor is programmed to analyse said audio signal by mapping successive segments of said audio signal to a set of features selected from a dictionary of said features.

The array of stimulators can be, for instance, a rectangular arrangement of m×n regularly spaced stimulators, a hexagonal arrangement of concentric hexagonal sub-arrays, or a circular arrangement of concentric circular sub-arrays.

Preferably, said processor is further operable to normalise the magnitudes of the actuation signals to fall within a predetermined range of actuation signal intensities.

In preferred embodiments, said tactile unit is in the form of a body dimensioned to be placed on the tongue of a human subject, and wherein each stimulator is in the form of an electrode having a rounded surface projecting from said body.

More preferably, the rounded surface of each electrode is generally hemispherical.

The preferred embodiment uses a tongue-based electrode array as an auditory sensory substitution device, whereby audio information is presented to the brain by way of tactile stimulation applied to the tongue. The system is composed of a wireless electro-tactile display device and an audio processing computer, which wirelessly transmits electro-tactile stimulus images to be displayed—using Bluetooth technology to the electro-tactile display. Alternatively, both components can be combined into a single unit for added portability. Furthermore, the tactile stimulus generated by the system may be presented to any cutaneous surface on the body for that matter.

DETAILED DESCRIPTION OF PREFERRED EMBODIMENTS

Figure 1:
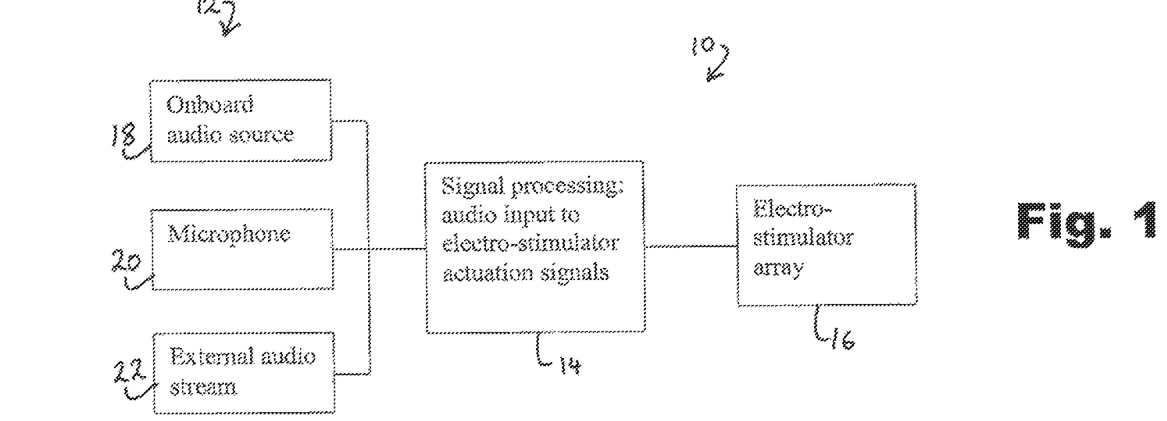
FIG. 1 shows an apparatus for treating tinnitus comprising one or more of a plurality of audio input sources, a signal processing module, and an electro-stimulator array.

Referring to FIG. 1 there is indicated, generally at 10 an apparatus for treating tinnitus, which comprises one or more of a plurality of audio input sources 12, a signal processing module 14, and an electro-stimulator array 16.

The audio source(s) can be of any type, and for illustrative purposes, FIG. 1 shows three such options: an onboard audio source 18, such as a set of MP3 files and an integrated audio decoder, a microphone 20 for receiving ambient sound signals, or a connection to an external audio source 22 such as the sound card of a computer. The system may have a plurality of such sources, for example a built-in audio source for use in training or active treatment sessions, a microphone for processing sounds in the external environment of the user, and an input jack (e.g. a standard 3.5 mm jack) for connection to external audio sources. Other input methods such as a proprietary iPod connector, or a connector for another MP3 player, or an optical audio input, may of course be provided (iPod is a trade mark of Apple Inc. of Cupertino, Calif.).

Figure 2:
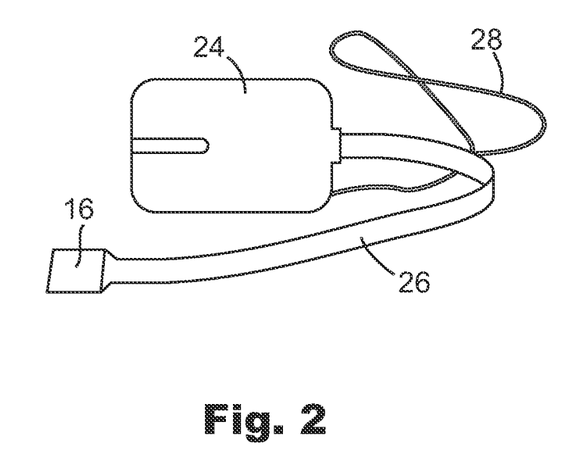
FIG. 2 shows a physical embodiment of an apparatus for treating tinnitus.

FIG. 2 shows a physical embodiment of such as system, which comprises a housing 24 containing an onboard audio source 18 and signal processing module 14 (FIG. 1, not shown in FIG. 2), an electrostimulator array 16 having a 16×16 array of electrodes on a 9.lbstrate sized to be placed on the human tongue, a connector ribbon 26 which carries 256 individual actuation signals from the housing 24 to the individual electrodes of the array 16, and a lanyard 28 for hanging the housing around a subject's neck.

Figure 3:
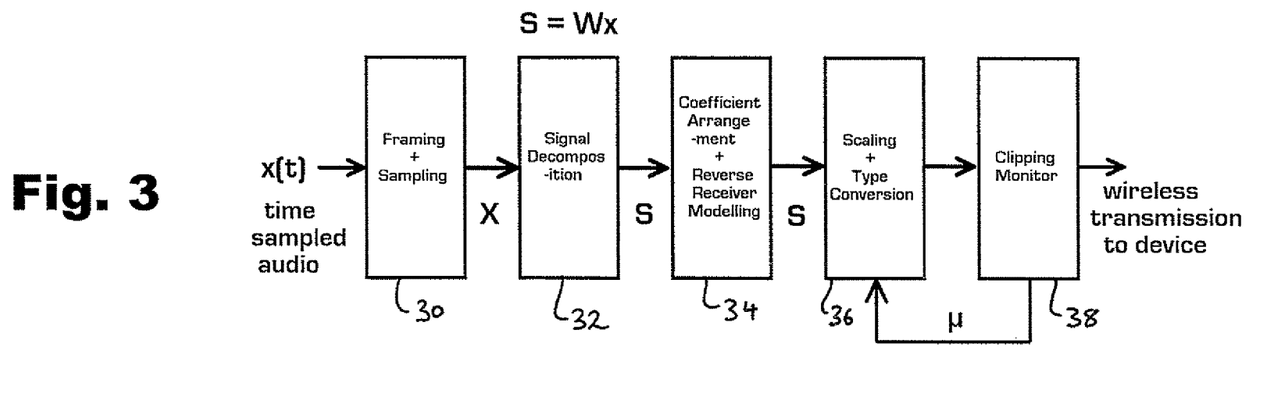
FIG. 3 shows the signal processing module of FIG. 1 comprising a sampling and framing module, a signal decomposition and analysis module, coefficient arrangement and reverse receiver modelling module, a scaling and type conversion module and an clipping monitoring module.

Referring now to FIG. 3, the audio input is processed by the signal processing module 14 of FIG. 1, which produces the necessary set of 256 actuation signals to represent the audio input. The signal processing module 14 has the following functional modules, each of which will be described below in further detail: an audio input signal x(t) received as a time-sampled signal is subjected to sampling and framing 30, then to a signal decomposition and analysis process 32, giving a set of coefficients or symbols representative of the sound which are subjected to spatial arrangement of coefficients and reverse receiver modelling 34, followed by scaling of coefficient values and type conversion 36, and an iterative clipping monitoring and correction process 38.

Sampling & Framing

Figure 4:
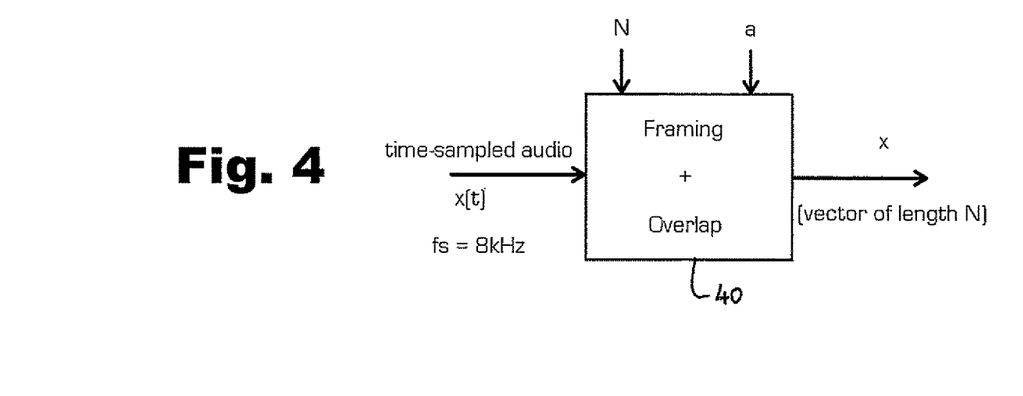
FIG. 4 shows the framing and overlap module which forms part of the sampling and framing module of FIG. 3.

Referring to FIG. 4, the system receives time-sampled audio x(t). The time-sampled data is arranged into chunks known as frames in a framing and overlap function 40 which forms part of the sampling and framing function 30 of FIG. 3. We denote a single frame using matrix notation as x, where subsequent processing is applied to each frame individually—as opposed to processing the entire audio stream at once.

As is typical with audio analysis, it is necessary that the specified frame size (i.e., analysis window length) is consistent with the duration of audio objects contained in the audio under consideration; e.g., speech phonemes, musical notes. The frame size—which is measured in samples and we denote N—depends on the sampling rate and is typically a power of two. Moreover, it is desirable to ameliorate frame boundary effects using a windowing function, we specify a Hamming window function. Frames are not restricted to be contiguous in the audio stream and may overlap. For our embodiment we chose a sampling rate, fs, of 8,000 Hz, which corresponds to a signal bandwidth of 4,000 Hz, which is known to capture sufficient frequency information such that the reconstructed signal is intelligible as audio. From our analysis of the TIMIT speech corpus—including both male and female sentences—we used the following statistics pertaining to phoneme length as a guide for frame size: Maximum length=164 ms, minimum length=18 ms, average length=81 ms, median length=67 ms—we keep in mind a frame size of 512 (64 ms) or 1024 (128 ms) audio samples.

A possible alternative would be a non-frame-based streaming embodiment, in which a succession of nonlinear filters extract desired information from the input audio waveform with the features being sample-aligned or even subsample-aligned, rather than being restricted to or aligned with frame boundaries. In this scenario, N may equal a single sample.

In the context of the electro-tactile array display device, each frame will produce a single electro-tactile array "image" (or output array pattern), which is to be displayed on the device. Consecutive frames create a sequence of such images, and is analogous to displaying a movie on a television screen. For our system, we used an array that contains 16×16 electrodes, where each electrode has a dynamic range of 0 to 255 voltage levels, which corresponds to an unsigned char data type in the C programming language. As discussed above, the sample rate is largely dependant on the bandwidth of the signals under consideration. However, the refresh rate of the electro-tactile display also has to be considered: taking a television screen as an example—which exploits persistence of vision—if the refresh rate is too low there are noticeable jumps between scenes. Similarly, with the electro-tactile display, if the refresh rate is too low there may be a lack of continuity between consecutive images and the presented information will exhibit similar jumps between frames. Conversely, if the rate is too high, consecutive individual frames may be perceived as one—due to the sensory bandwidth limits of the tongue—and will achieve no benefit. In short, there is a tradeoff between sampling frequency and the refresh rate of the device, which is dependant on the array/image size.

For the system, we specified an image frame rate (display refresh rate) of 62.5 frames per second, which is consistent with persistence of vision, and decided on a frame size of 512 samples (here the frame size is twice the array size; below we discuss how 256 coefficients are generated for the array using the magnitude spectrogram).

Furthermore, in order to achieve consistent stimulus patterns between consecutive electro-tactile images, overlapping of frames is necessary; where frames of length N overlap by o samples, where every a=N−samples the analysis window slides to include the new samples, at which point a frame is processed and a new image is generated and transmitted to the display. Therefore the display is updated every a samples, where a represents a frame advance (as opposed to overlap).

We specify a frame rate of 62.5 Hz, which at a sample rate of 8 kHz corresponds to 16 ms duration. However, since the frame size is of 64 ms duration (so that the audio objects can be captured) we overlap frames as recommended previously where N=512 and a=128, which satisfies the frame rate duration of 16 ms.

Finally, we summarise using the following quantitative illustration: we update the array at 62.5 Hz, and wish to include frequencies up to 4,000 Hz. With this as the Nyquist frequency, this implies a sampling rate of 8 kHz. We use frames that hold 4 updates, meaning that each frame holds:

4 updates/frame×8,000 samples/s=512 samples/frame
62.5 updates/s with frames overlapped so that a new frame is created every update, which here would be every 128 samples Since the frames size is 512 and the array size is 256 (remember a frame corresponds to an array image) we generate a 256 coefficient representation to be displayed on the array by using an appropriate signal decomposition as discussed below.

Signal Decomposition and Analysis

Since the introduction of information theory in the middle of the last century (Shannon, 1948), it has been suggested that the redundancy of sensory inputs is important for understanding perception (Attneave, 1954; Barlow, 1959). The redundancy contained in our surroundings is what enables the brain to build up cognitive models of environment around it (Barlow, 1961, 1989). It is thought that statistical regularities in sensory inputs must somehow be separated from redundancies and be encoded in some efficient way, this has led to Barlow's hypothesis, which states that the purpose of early perceptual processing is to transform the highly redundant sensory input into a more efficient factorial code, which can be stated as the following matrix transformation, $$S = Wx \qquad \text{Equation 1}$$

where $W=[w1|\ldots|wN]$ is an N×N linear matrix operator, $x=[x1,\ldots,xN]T$ is the sensory input vector and $s=[s1,\ldots,sN]T$ is the encoded input, where the values of W,s,x are real numbers, i.e. $W, s, x \in R$ Such a transformation is performed by a matrix-vector multiply operation, and can be used in auditory sensory substitution, where x above corresponds to our frame, and s is the encoded output, which is to be represented as voltages on an electro-tactile display.

Figure 5:
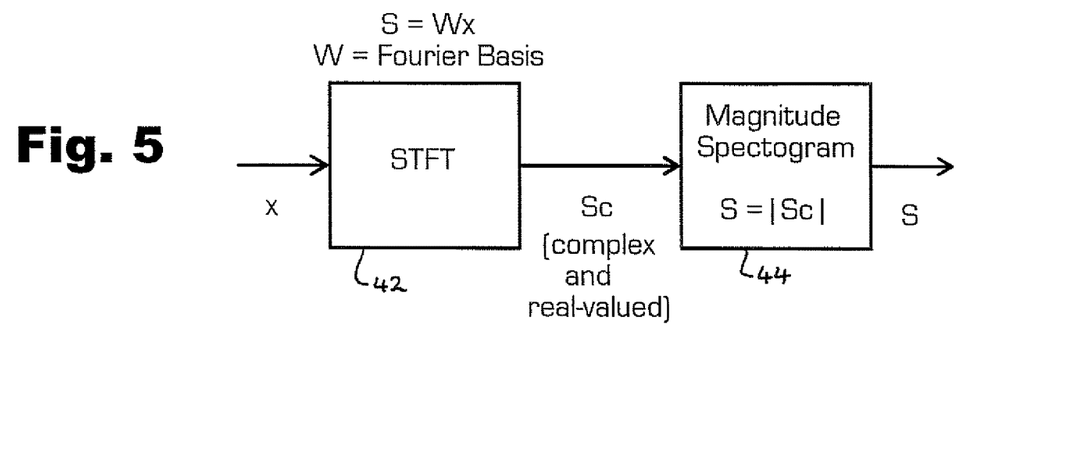
FIG. 5 shows a harmonic analysis (Discrete Short-Time Fourier transform (STFT)) module and a magnitude spectrogram.

Referring to FIG. 5, we decompose the audio stream (after sampling and framing) into the superposition of basic waves by way of Harmonic Analysis. The most common kind of Harmonic Analysis is Fourier analysis by way of the discrete short-time fourier transform (STFT), i.e., decomposition of a signal into sine waves, where W corresponds to a Fourier basis in the complex domain, C, which yields a complex valued $s \in C$ that we denote $s_c$. The STFT function is represented symbolically by the function 42 in FIG. 5.

In order to transform the coefficients, $s_c$, to a form suitable for display on the electro-tactile array, we employ a magnitude spectrogram 44 of the resultant STFT coefficients, and display those values. An additional advantage of using the magnitude spectrogram is that the resultant coefficients, $s_n$ are non-negative (i.e., exclude negative values, s≥0);

$$s_n = mag(s_c) \qquad \text{Equation 2}$$

Negative values cannot be displayed on the electro-tactile array, since the electrode voltages represent intensity, therefore the coefficients to be displayed on the device must be in the form $s_n$.

Since the STFT results in symmetric values, only the first half of the STFT frame is required to generate the magnitude spectrogram, resulting in 256 coefficients to be displayed on the array, one for each electrode.

Together the STFT function 42 and the magnitude spectrogram function 44 provide the generalised signal decomposition function 32 shown in FIG. 3.

Other possible alternatives include generalised notions of Fourier analysis such as Wavelet transforms, Gammatone transforms, Zak transforms, Curvelet transforms etc, can also be used to represent audio on the electro-tactile array by replacing W with the bases that defines these transforms.

As evidenced by the pilot trials with 20 tinnitus patients (described further below) using the system of FIGS. 1 and 2, it is evident that over time a subject learns to associate the stimulus (magnitude spectrogram coefficients) presented by the electro-tactile display to the tongue with individual sounds. The premise of the treatment is that the somatosensory cortex—which receives tactile information from the tongue—has sufficient pathways to the auditory cortex to make this correlation.

In the context of this tinnitus treatment, since the brain has no other external reference for the audio environment, we demonstrate through our trials that providing an additional reference for the audio environment by way of audio sensory substitution enables the brain to recalibrate compensatory mechanisms through brain plasticity, thus ameliorating the effects of tinnitus.

Spatial Arrangement of Coefficients

Since audio is a one-dimensional signal and we wish to display it on a two dimensional electro-tactile array, it is necessary to perform an embedding of the one dimensional data into two dimensional space. The output from the signal decomposition stage is also one dimensional. Finding an appropriate topology is an offline task, where the resultant arrangement is represented by an N×N permutation matrix P. During runtime the coefficients $s_n$ are rearranged by performing a matrix multiplication with the permutation matrix, $$s_n = Ps_n \qquad \text{Equation 3}$$

In the context of signal decomposition using a Fourier Basis, we preferably arrange the vectors tonotopically, i.e., where components close to each other in terms of frequency are placed in proximity to each other on the array. Where (0,0) in matrix notation (top left) corresponds to the highest frequency component, while $(\sqrt{N},\sqrt{N})$ (bottom right) corresponds to the lowest frequency component. Essentially, the frame is split into $\sqrt{N}$ vectors, which are then used to construct the rows of the matrix/image to be displayed on the electro-tactile array.

Reverse Receiver Modelling and Signal Shaping

Figure 6:
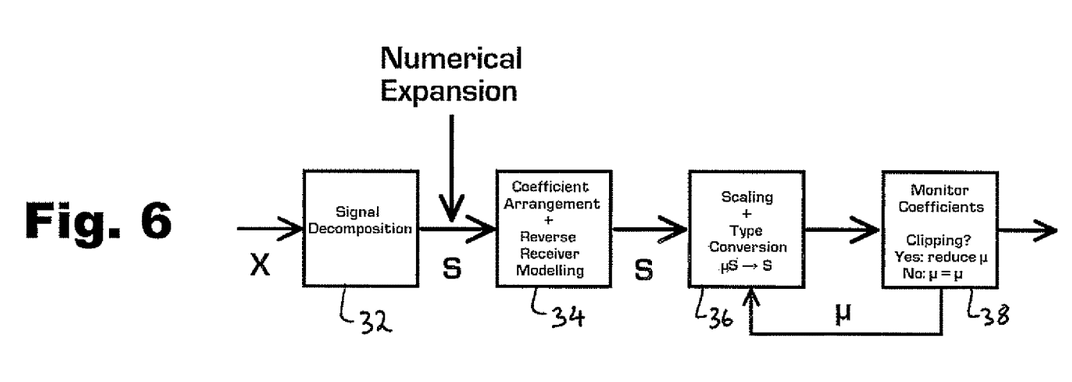
FIG. 6 shows post processing after signal decomposition.

Referring to FIGS. 3 and 6, following signal decomposition and coefficient arrangement, it can be necessary to perform post-processing on the resultant signal activations so as to shape them into a suitable form so that audio can be more readily perceptible through the tongue, as represented at 36.

For example, in the context of audio post-processing, it is sometimes necessary to compress the dynamic range of the audio (using a non-linear function), which narrows the difference between high and low audio levels, so that quiet signals can be heard in noisy environments. It may be necessary to shape the signals presented to the electro-tactile display in a similar way, so as to ensure that the tongue is capable of hearing all the signals in the audio following decomposition. At its most basic level, such signal shaping performs amplification of stimulus on a per-electrode level based on sensitivity of the tongue in that region to such stimulus.

An important consideration when transforming time-sampled audio into another domain by way of basis transformation (Equation 1) is that the resultant coefficients experience a numerical expansion, which by-and-large is indeterminate. For example, our audio input is normalised to between −1 and +1 when it comes from the sound card. However, a signal decomposition of the waveform may produce values that are greater than this range, this behaviour is termed numerical expansion. This is represented in FIG. 6 as occurring between signal decomposition 32 and coefficient arrangement 34.

Ultimately, the coefficients will be represented on the array, where each electrode has the dynamic range of an unsigned char type (0 to 255). To ensure that the coefficients fit within this range it is necessary to perform scaling of the coefficients—either before or after signal decomposition—so that the coefficients to be displayed, will not result in clipping on the electro-tactile array after conversion to an unsigned char type, i.e., the coefficients to be displayed don't exceed the dynamic range of the electrodes. Therefore, scaling/normalisation, e.g. sµ→s where µ is the scaling factor, is required to ensure that the coefficients to be displayed on the device reside in the dynamic range of the electrode voltage intensity.

Audio processing is performed using a double precision floating point number (8 bytes). However, the electrodes on the array can represent 0-255 voltage intensities (1 byte), which corresponds to a unsigned char. Coefficient monitoring and scaling ensures that the coefficients (double type) reside in the range 0->1, which are then converted to unsigned chars for presentation on the array by multiplying by 255.0 then casting the coefficient variable to an unsigned char. This process is iteratively shown between processes 36 and 38, and is referred to as "type conversion" at 36.

The typical procedure is to determine an appropriate scaling value for the signal in an ad hoc fashion, then monitor the values of the resultant coefficients, s, decreasing the value µ by a small amount if clipping occurs; the scaling value quickly stabilises to a suitable value.

Furthermore, perceptual effects also need to be considered. For example, the MP3 audio compression standard is a lossy audio compression method where sounds that are imperceptible by the human ear (due to perceptual masking of such sounds) are removed from the audio with little perceptible difference from the point of view of the listener. The MP3 standard employs a "reverse receiver model" where signals that the receiver (human ear) cannot perceive are removed by the MP3 codec with no/little degradation in quality of the perceptible signal. Such perceptual masking effects will most definitely be exhibited by the area of the body to which the tactile array is applied (e.g. tongue) and can be exploited when displaying information on the electro-tactile display.

Electro-Tactile Array

The electrode array employed in the device of FIG. 2 uses hemispherical electrocutaneous stimulators ensuring homogeneous electrode-skin interface current density. Electrostatics dictates that the distribution of charge on the surface of a charged body is greatest at areas of greatest surface curvature. This is commonly known as the 'edge effect'. Charged bodies with sharp edges experience charge build up along those edges. Most electrocutaneous stimulators use flat disc-like electrodes. Microscopic inspections of these electrodes reveal sharp edges at the electrode perimeter. It has been shown that these edges experience unequal current distribution at the electrode-skin interface during electrocutaneous stimulation (Krasteva and Papazov, 2002). This will affect the qualitative perception of the stimulus and may even cause pain or skin burn.

Gauss' Law for the field strength outside a sphere of radius R is $$E = Q/4\pi\epsilon R^2 \qquad \text{Equation 4}$$

and charge density D (charge per unit surface area) on a sphere of radius R for a charge Q scales similarly:

$$D = Q/4\pi R^2 \qquad \text{Equation 5}$$

In our setting, these equations mean that field strength and charge density D are inversely proportional to the electrode radius R. Assuming constant charge Q, this implies that field strength and charge density will be greater at the point of a pin than on the surface of a large sphere.

This implies that that for a given electrode size, if we wish to minimise the maximum field strength, the electrode should be spherical.

Current density is given by the equation:

$$J(r,t) = qn(r,t)v_d(r,t) \qquad \text{Equation 6}$$

where J(r,t) is the current density vector at location r at time t (SI unit amperes per square meter). n(r,t) is the particle density in count per volume at location r at time t (SI unit m−3) is the charge of the individual particles with density n (SI unit: Coulomb). We employ a hemispherical electrocutaneous stimulator with a uniform radius and surface curvature that will ensure homogeneous current density at the electrode-skin interface, thus reducing the risk of painful current concentrations.

A uniformly distributed hexagonal electrode array consists of concentric hexagonal arrays with uniformly distributed electrodes. The number of electrodes e is given by the following equation:

$$e = 1 + \sum_{n=1}^{k} 6n = 1 + 3k(k+1) = 3k^n + 3k + 1$$

where k is the number of concentric hexagonal arrays in the array around the centre electrode. The advantage of this array is that the intra-electrode spacing is uniform across the array.

Pilot Trials

We enrolled 20 participants to partake in a four-week trial of a treatment device which simultaneously presented sound to the modalities of hearing and touch. Music that is played to the user through headphones is simultaneously decomposed into constituent waveforms (using the STFT transform method described above) that are encoded into tactile patterns and presented to the user through an intra-oral electrotactile sensor placed on the tongue.

The treatment was provided to 12 males and 8 females with an average age 48±22 years with permanent tinnitus (persistent symptoms >6 months) due to noise and/or age related hearing loss. Participants were not receiving any other treatment for their hearing loss or tinnitus.

The treatment regimen consisted of using the device for 30-mins in the morning and again in the evening. In each treatment session, participants listened to 30 minutes of prescribed music in the headphones, while simultaneously feeling the tactile representations of the music on the tongue.

Participants were assessed pre- and post-intervention using the Tinnitus Handicap Inventory (THI) [see C. W. Newman et al., *Arch Otolaryngol Head Neck Surg.*, vol. 122, pp. 143-148, 1996; and A. McCombe et al., *Clin Otolaryngol*, vol. 26, pp. 388-393, 1999], and using the Tinnitus Reaction Questionnaire (TRQ) [see P. H. Wilson et al., *Journal of Speech and Hearing Research*, vol. 34, pp. 197-201, 1991.]. The Tinnitus Handicap Inventory is a self-report tinnitus handicap measure that quantifies the impact of 25 aspects of tinnitus on daily living. The THI categorises inventory scores into 5 severity grades: Grade 1: Slight, 2: Mild, 3: Moderate, 4: Severe and 5: Catastrophic. The pre-intervention THI measure was used to assess the impact of tinnitus on the participant in the four-week period prior to the beginning of the study. The post-intervention measure was used to assess the impact of tinnitus on the participant in the four-week period that the participant was receiving the treatment.

The Tinnitus Reaction Questionnaire is a self-report tinnitus reaction measure that assesses 26 aspects of tinnitus on quality of life. A TRQ score of 16 or greater is considered clinically significant. The pre-intervention TRQ measure was used to assess the impact of tinnitus on the participant in the one-week period prior to the beginning of the study. The post-intervention measure was used to assess the impact of tinnitus on the participant in the one-week period prior to the completion of the study.

In addition to the THI and TRQ, participants were asked to describe any symptomatic changes and state if the symptoms were Gone/Greatly Improved/Improved/Unchanged/Worse/Worst.

Participant compliance: out of the 20 participants recruited for the study, 17 successfully completed the four weeks of treatment.

Over 60% of the participants that completed the four-week treatment reported that their symptoms had 'Improved' or 'Greatly Improved'.

Almost 60% of participants registered a reduction of one grade or more in their THI scores.

Almost 90% of participants registered improvement in the TRQ scores with 65% registering improvements greater than 20%. 30% of participants transitioned from clinically significant TRQ scores (>16) to non-clinically significant TRQ scores (<16).

Possible Alternative Signal Decompositions

Since the premise for our signal decomposition step is based on the general notion of exploiting redundancy in sensory inputs, signal decomposition is not restricted to harmonic analysis due to the fact that many different assumptions can be used to achieve Equation 1. In the following sections we describe possible alternatives for this step.

While harmonic analysis methods are extremely useful, it is possible to construct more parsimonious representations using features (which are called a signal dictionary or basis vectors) that are learned from a corpus of data. Such parsimonious or sparse methods create representations with fewer active coefficients and produce better images that can be displayed on the array. Parsimonious representations are common in signal analysis/processing and are typically used to make a signal compressible, e.g., Discrete Cosine Transformations are used in MPEG video compression.

The learning step is performed off-line, i.e., a priori, while the decomposition of the input audio stream (fitting) to the discovered dictionary is performed in real-time. Below we outline a number of such approaches that can be used to construct a signal dictionary that is tuned to a corpus of sound, e.g., speech.

When learning signal dictionaries it is necessary to apply the method chosen to some training data (e.g., speech, music, audio in different environments etc.) off-line, where the training data is sampled and framed using the same scheme described previously, however, a sequence of K frames are considered at once and we use $X=[x1|\ldots|xK]$ to denote the training data matrix. The resultant signal dictionary, W, produces encodings, s, that are optimised for the training data, which can be used to produce optimal encodings for these type of data—provided that K is large enough. For example, when listening to music at an outdoor event, it is useful to use a signal dictionary that is learned from recordings of outdoor music events (as opposed to say whale music) in order to achieve a parsimonious encoding.

In Equation 1, W is constructed from this pre-calculated signal dictionary and when sound is presented to the system it is encoded using this dictionary matrix. The coefficients of the resultant encodings, $s1, \ldots, sN$, are topologically organised depending on some criterion (e.g., mutual dependencies between $s1, \ldots, sN$) and are represented on the electrotactile display. Such an organisation is similar to the tonotopic organisation of auditory receptors in the auditory cortex. In this way, the system performs the perceptual encoding of dysfunctional modality.

The following methods learn W from a corpus of data, X, in an offline fashion, x are subsequently projected onto the fixed signal dictionary W by way of a linear transformation (Equation 1) in real-time when the system is operational.

Principal Component Analysis

Principal Component Analysis (PCA) (Pearson, 1901) (also known as the Karhunen-Lo' eve transform or the Hotelling transform) is a technique for the dimensionality reduction of multivariate data—X is multivariate—which retains the features of the data that contribute most to its statistical variance. PCA is a linear transformation that does not have a fixed set of basis vectors (unlike the Fourier Transform for instance). Instead, PCA transforms the training data X to an orthogonal coordinate system that corresponds to the directions of the variance of the data. The vectors that define the directions of variance, $[w1|\ldots|wN]$, are known as the principal components of the data:

$$\Sigma_X = W\Lambda W^{-1} \qquad \text{Equation 7}$$

where $\Sigma_X = \langle XX^T \rangle$ is the covariance matrix of X and the input to the learning stage. After learning, i.e., has been diagonalised into the form of Eq. 7, W contains the eigenvectors (principal components) of $\Sigma_x$ and the diagonal matrix $\Lambda$ contains its associated eigenvalues $\lambda i \ldots \lambda N$. During runtime when a frame x—from the same class of audio data—is projected on to W (Eq. 1), then the variates of the s, $s1, \ldots, sN$, are (approximately) decorrelated, i.e., the correlation matrix for s is a diagonal matrix. In this way, the decorrelated components of sound can be displayed on the device.

Independent Component Analysis

Independent Component Analysis (ICA) (Comon, 1994) encompasses a range of methods for the separation of multivariate data into statistically independent components. Inspired by Barlow's hypothesis, (Atick and Redlich, 1990) postulated the principal of minimum redundancy, which proposes a model that utilises such a method as the mechanism to achieve an efficient code. ICA provides a linear matrix operator, W, (which is learned from training data X) that factors the joint probability distribution of s into independent components, $$P(s) = P(s_1, \ldots, s_N) = \prod_{i=1}^{N} P(s_i) \qquad \text{Equation 8}$$

and is generally solved as an optimisation problem, where W is discovered by maximising some measure of independence. Such measures include mutual information (Comon, 1994), entropy (Bell and Sejnowski, 1995), non-gaussianity (Hyvarinen and Oja, 1997), and sparseness (Zibulevsky and Pearlmutter, 2001). By using a signal dictionary, W, constructed by ICA in Equation 1, it is possible to display the statistically independent components of sound, which produces encodings that are both decorrelated and mutually independent.

Non-Negative Matrix Factorisation (NMF) is linear non-negative low-rank approximative factorisation for the decomposition of multivariate data (Lee and Seung, 2001; Paatero and Tapper, 1994). NMF is a parts-based approach that makes no statistical assumption about the data. Instead, it assumes that for the domain at hand—for example grey-scale images—negative numbers are physically meaningless. Negative components have no real-world representation in a grey-scale image context, which has led to the constraint that the search for W should be confined to a non-negative values, i.e. values greater than and including zero. Data that contains negative components, e.g., sound, must be transformed into a non-negative form before NMF can be applied. Typically, the magnitude spectrogram is used for this purpose, where the training data X also undergoes the magnitude spectrogram process as outlined above. Formally, NMF can be interpreted as $$\min_{A,S} \frac{1}{2}\|X - AS\|^2, \qquad \text{Equation 9}$$

$$A, X, S \geq 0$$

where $A = W^{-1}$ is an N×R matrix with R≤N, such that the reconstruction error is minimised. The factors A and S are learned from the training data X using multiplicative update rules (Lee and Seung, 2001), where A contains the features of the data and S their activations, which are discarded after the learning step. NMF encodings are non-negative, and as such are readily available for display, whereas the encodings produced by PCA and ICA may include negative components, which require an additional non-linear transformation (e.g., absolute value) before they can be displayed.

During runtime, each frame x results in $s_n$ by performing the following optimisation, $$\min_{A,s} \frac{1}{2}\|x - As_n\|^2, \qquad \text{Equation 10}$$

$$A, x, s_n \geq 0$$

Sparse Overcomplete Decomposition

In Equation 1, the dictionary into which the input sound x is being decomposed, i.e., the columns of W−1, has a size equal to (or less than) the dimensionality N of x. As discussed, it can be desirable for the decomposition of x to be sparse, meaning that it is to be expressed in terms of a small number of dictionary elements, which corresponds here to the vector s being sparse. If the distribution from which x is drawn is sufficiently rich, this can be impossible with any dictionary with only N elements.

As an alternative, one can use an overcomplete dictionary, meaning that it has more than N elements, i.e., the signal dictionary is a fat matrix. If the dictionary is placed in the columns of a matrix D then this corresponds to finding a vector s which is sparse, and which also satisfies the under-constrained equation Ds≈x.

Up to this point we have described using Equation 1 to transform x using the signal dictionary. We now specify an overcomplete signal dictionary D, where transformation using Equation 1 is not possible since the equation is under-constrained for D, we therefore use the optimisation Equation 11 below to achieve the transformation.

There are a variety of algorithms for finding such a vector s, the most prominent of which is L1 decomposition, in which an s is found whose elements with a minimal sum of absolute values subject to the above condition where the ≈ is made concrete as squared error, resulting in:

$$\min_{s} \sum_{i=0}^{M} |s_i| + \lambda \|Ds - x\|_2^2 \qquad \text{Equation 11}$$

where λ is a constant that trades off the sparseness of s against the fidelity of the representation of x.

Just as is the case for W in Eq. 1, the dictionary D can be found by a variety of means, including PCA, ICA, NMF and variants thereof, such as overcomplete ICA and sparse convolutive NMF (O'Grady and Pearlmutter, 2008).

Furthermore, it is possible to combine signal dictionaries that are trained on different data and construct an overcomplete dictionary. For example, using ICA we can construct two signal dictionaries the same dimension as W for speech, where one is tuned to male speech, which we denote M, and the other tuned to female speech, which we denote F. We can then combine both to construct D, where D=[M|F]. The advantage being that when male speech is captured in the audio stream the M portion of D is most active giving sparse representations, and vice versa.

As noted earlier, the electrodes on the electro-tactile display represent intensity and therefore the coefficients to be displayed on the device, $s_n$, must be non-negative. For the alternative methods described above—with the exception on NMF and the magnitude spectrogram—it is necessary to pass the resultant coefficients, s, through a non-linearity that produces only non-negative values in the output. We use the absolute value of s to generate $s_n$, $$s_n = \text{abs}(s) \qquad \text{Equation 12}$$

To represent dictionary elements describing the audio signal on a 2 dimensional array, the dictionary elements used to decompose the signal, which are of length N, can be thought of as points in N space, with different distances between each vector. It is possible to embed these multi-dimensional vectors into two-dimensional space, and hence achieve a two dimensional arrangement, using methods such as Locally Linear Embedding or Multi-dimensional scaling. These methods require a distance (or divergence) measure, which may be determined either directly from the dictionary elements, or using statistics of their response properties. This would mean exploiting the statistics of these vectors, thus arranging vectors that have similar statistics—such as cross-correlation, relative entropy, mutual dependence etc—in close proximity.

The invention claimed is:

1. An apparatus for use in treating tinnitus, comprising a sound processing unit, a tactile unit, and an interface therebetween, wherein:
   said tactile unit comprises an array of stimulators each of which can be independently actuated to apply a tactile stimulus to the tongue of a user, and an input for receiving a plurality of actuation signals from said interface and directing individual actuation signals to individual stimulators; and
   said sound processing unit comprises:
   an input for receiving an audio signal; a digital signal processor operable to analyze said audio signal and generate said plurality of actuation signals therefrom which are representative of said audio signal; and
   an output for receiving said plurality of actuation signals from said digital signal processor and providing said plurality of actuation signals to said interface.

2. An apparatus as claimed in claim 1, wherein said digital signal processor is further operable to generate said plurality of actuation signals as a time-varying sequence of output array patterns, wherein each output array pattern comprises a set of actuation signals to be applied to the array for a discrete period of time, representative of a discrete time sample of the input signal.

3. An apparatus as claimed in claim 1, wherein said digital signal processor is programmed to analyse said audio signal by dividing said audio signal into a series of frames in the time domain, performing a transform on each frame to generate a set of coefficients representing said frame, and mapping said set of coefficients to a set of actuation signals to be applied to the array.

4. An apparatus as claimed in claim 3, wherein said transform performed on each frame is selected from a Fourier transform, a short-time Fourier transform (STFT), a wavelet transform, a curvelet transform, a gammatone transform and a zak transform.

5. An apparatus as claimed in claim 4, wherein said transform is a Fourier transform or a short-time Fourier transform, and wherein said signal is sampled at a sampling rate of between 4 kHz and 12 kHz.

6. An apparatus as claimed in claim 3, wherein said time-varying series of frames overlap with one another.

7. An apparatus as claimed in claim 3, wherein the start of each frame is offset from the start of the preceding frame by between 10 and 20 ms.

8. An apparatus as claimed in claim 3, wherein said processor is programmed to employ a frame length of from 18 to 164 ms.

9. An apparatus as claimed in claim 3, wherein said set of coefficients represents the signal in the frequency domain, and wherein the coefficients are mapped to the actuation signals such that coefficients representing similar frequencies are mapped to actuation signals directed to stimulators which are physically close to one another in said array.

10. An apparatus as claimed in claim 9, wherein coefficients representing neighbouring frequencies are mapped to actuation signals directed to stimulators which are physically adjacent to one another.

11. An apparatus as claimed in claim 1, wherein said digital signal processor is programmed to analyse said audio signal by mapping successive segments of said audio signal to a set of features selected from a dictionary of said features.

12. An apparatus as claimed claim 1, wherein said array of stimulators is a rectangular arrangement of regularly spaced stimulators.

13. An apparatus as claimed in claim 1, wherein said array of stimulators is a hexagonal arrangement of concentric hexagonal sub-arrays.

14. An apparatus as claimed in claim 1, wherein said array of stimulators is a circular arrangement of concentric circular sub-arrays.

15. An apparatus as claimed in claim 1, wherein said digital signal processor is further operable to normalise the magnitudes of the actuation signals to fall within a predetermined range of actuation signal intensities.

16. An apparatus as claimed in claim 1, wherein said tactile unit is in the form of a body dimensioned to be placed on the tongue of a human subject, and wherein each stimulator is in the form of an electrode having a rounded surface projecting from said body.

17. An apparatus as claimed in claim 16, wherein the rounded surface of each electrode is generally hemispherical.

* * * * *